(12) United States Patent
Valint, Jr. et al.

(10) Patent No.: US 7,988,988 B2
(45) Date of Patent: Aug. 2, 2011

(54) CONTACT LENSES WITH MUCIN AFFINITY

(75) Inventors: Paul L. Valint, Jr., Pittsford, NY (US);
Joseph A. McGee, Dewitt, NY (US);
David P. Vanderbilt, Webster, NY (US);
Joseph C. Salamone, Boca Raton, FL (US)

(73) Assignee: Bausch & Lomb Incorporated, Rochester, NY (US)

( * ) Notice: Subject to any disclaimer, the term of this patent is extended or adjusted under 35 U.S.C. 154(b) by 1006 days.

(21) Appl. No.: 11/283,632

(22) Filed: Nov. 21, 2005

(65) Prior Publication Data
US 2007/0116740 A1    May 24, 2007

(51) Int. Cl.
*G01N 1/18* (2006.01)
*A61F 2/00* (2006.01)
*A61F 35/32* (2006.01)
*A61F 35/36* (2006.01)

(52) U.S. Cl. ........................ 424/427; 427/574
(58) Field of Classification Search ................ None
See application file for complete search history.

(56) References Cited

U.S. PATENT DOCUMENTS

| | | | |
|---|---|---|---|
| 4,136,250 A | 1/1979 | Mueller et al. | |
| 4,153,641 A | 5/1979 | Deichert et al. | |
| 4,634,722 A | 1/1987 | Gallop | |
| 4,740,533 A | 4/1988 | Su et al. | |
| 4,910,277 A | 3/1990 | Bambury et al. | |
| 5,034,461 A | 7/1991 | Lai et al. | |
| 5,070,215 A | 12/1991 | Bambury et al. | |
| 5,260,000 A | 11/1993 | Nandu et al. | |
| 5,310,779 A | 5/1994 | Lai | |
| 5,346,976 A | 9/1994 | Ellis et al. | |
| 5,358,995 A | 10/1994 | Lai et al. | |
| 5,387,662 A | 2/1995 | Kunzler et al. | |
| 5,407,919 A | 4/1995 | Brode et al. | |
| 5,449,729 A | 9/1995 | Lai | |
| 5,512,205 A | 4/1996 | Lai | |
| 5,595,980 A | 1/1997 | Brode et al. | |
| 5,610,252 A | 3/1997 | Bambury et al. | |
| 5,616,757 A | 4/1997 | Bambury et al. | |
| 5,708,094 A | 1/1998 | Lai et al. | |
| 5,710,302 A | 1/1998 | Kunzler et al. | |
| 5,714,557 A | 2/1998 | Kunzler et al. | |
| 5,908,906 A | 6/1999 | Kunzler et al. | |
| 5,985,629 A | 11/1999 | Aaslyng et al. | |
| 6,200,626 B1 * | 3/2001 | Grobe et al. | 427/2.24 |
| 6,213,604 B1 | 4/2001 | Valint, Jr. et al. | |
| 6,348,508 B1 | 2/2002 | Denick, Jr. et al. | |
| 6,440,571 B1 | 8/2002 | Valint, Jr. et al. | |
| 6,550,915 B1 | 4/2003 | Grobe, III | |
| 6,589,665 B2 | 7/2003 | Chabrecek et al. | |
| 6,649,722 B2 | 11/2003 | Rosenzweig et al. | |
| 6,794,456 B2 | 9/2004 | Grobe, III | |
| 6,815,074 B2 | 11/2004 | Aguado et al. | |
| 6,891,010 B2 | 5/2005 | Kunzler et al. | |
| 2004/0006385 A1 | 1/2004 | Valint, Jr. et al. | |
| 2004/0063591 A1 | 4/2004 | Borazjani et al. | |
| 2004/0063620 A1 | 4/2004 | Xia et al. | |

FOREIGN PATENT DOCUMENTS

| | | |
|---|---|---|
| WO | WO 99/10022 | 3/1999 |
| WO | WO 03/096876 A2 * | 11/2003 |
| WO | WO 2005/000109 A2 | 1/2005 |
| WO | WO 2005/015184 A1 | 2/2005 |

OTHER PUBLICATIONS

Springsteen et al., Tetrahedron, 2002, 58, 5291-5300.*
Sears et al., CMLS, 1998, 54, 223-252.*
Danjo et al., Investigative Ophthalmology and Visual Science, 1998, 39(13), 2602-2609.*
Otsuka et al., "Anomalous Binding Profile of Phenylboronic Acid with N-Acetylneuraminic Acid (Neu5Ac) in Aqueous Solution with Varying pH," Journal of American Chemical Society, vol. 125 ( No. 12), p. 3493-3502, (Feb. 27, 2003).
Kikuchi et al., "Glucose-Sensing Electrode Coated with Polymer Complex Gel Containing Phenylboronic Acid," Analytical Chemistry, vol. 68 ( No. 5), p. 823-828, (Mar. 1, 1996).

* cited by examiner

*Primary Examiner* — Sharmila G. Landau
*Assistant Examiner* — Kyle Purdy
(74) *Attorney, Agent, or Firm* — John E. Thomas (57) ABSTRACT

A biomedical device, such as a contact lens, has a surface linked to a polymer comprising boronic acid moieties. The boronic acid monomeric units may be derived from an ethylenically unsaturated monomer containing a boronic acid moiety, such as a vinylphenyl boronic acid or a (meth)acrylamido phenyl boronic acid. The boronic acid moieties may be complexed with mucin, especially epithelial mucin.

29 Claims, 1 Drawing Sheet

Figure 1

CONTACT LENSES WITH MUCIN AFFINITY

BACKGROUND OF THE INVENTION

Mucins are glycoconjugated proteins which are secreted by vesicles and discharged on the surface of the conjunctival epithelium of the eye. Mucins are found on moist, mucosal epithelia, and are thought to combine mechanical protection of eye tissue as well as chemical and immune protection of mucosal tissue. The surface of the eye is kept moist and lubricated by tear film. Mucins anchor this tear film to the epithelium and protect the eye surface from bacterial, chemical and physical invasion of foreign bodies.

U.S. Pat. Nos. 6,348,508 (Denick, Jr. et al.), 2004/0063620 (Xia et al.), and 2004/0063591 (Borazjani et al.) disclose compositions for treating dry eye or for treating contact lenses that comprise a cationic polysaccharide. In the case of eye drop solutions, the cationic polysaccharides, after binding to the mucosal eye tissue, may in turn promote the mucins in the eye, either by supplementing the mucin and/or by helping to bind and maintain mucin on the eye surface.

In the case of contact lenses, mucins are often viewed as a debris that, like other proteins, should not accumulate on the contact lens surface. For example, U.S. Pat. No. 5,985,629 (Aaslyng et al.) discloses contact lens cleaning and disinfecting compositions comprising an enzyme and an enzyme inhibitor. Aryl boronic acids are mentioned as a possible enzyme inhibitor and/or disinfectant, but the purpose of the compositions is to remove soil deposits from a contact lens, such soil deposits including mucin (at column 1). As another example, U.S. Pat. No. 6,649,722 (Rosenzweig et al.) discloses contact lens compositions. At column 28, it is reported that binding of mucin to the lens was at a desirably low enough level that the mucin would not lead to corneal adhesion of the lens.

SUMMARY OF THE INVENTION

This invention provides a biomedical device, especially an ophthalmic device such as a contact lens, comprising a surface linked to a polymer comprising boronic acid moieties. The boronic acid moieties may be monomeric units derived from an ethylenically unsaturated monomer containing a boronic acid moiety, such as a vinylphenyl boronic acid or a (meth)acrylamide phenyl boronic acid. The polymer may further comprise monomeric units derived from an ethylenically unsaturated hydrophilic monomer, monomeric units derived from an ethylenically unsaturated monomer containing a tertiary-amine moiety, and/or monomeric units derived from an ethylenically unsaturated monomer containing a reactive moiety. This reactive moiety reacts with complementary reactive functionalities on the lens surface or with complementary reactive functionalities on an intermediate polymer used to covalently link the boronic acid-containing polymer to the lens surface. The boronic acid moieties may be complexed with mucin, especially epithelial mucin.

This invention also provides a method comprising linking to a biomedical device surface a polymer comprising boronic acid moieties. In the case of an ophthalmic device, the device is placed on the eye, whereby mucin complexes with the boronic acid moieties. The invention includes a biomedical device comprising a copolymer covalently linked to a surface of the device, said copolymer comprising moieties that complex with mucin. The invention includes a biomedical device comprising boronic acid moieties that complex with mucin.

The invention includes a contact lens having greater affinity to epithelial mucin than to lysozyme. Additionally, various copolymers are provided by this invention.

DETAILED DESCRIPTION

This invention is useful for biomedical devices. The term "biomedical device" denotes a device that is placed into contact with tissue. This invention is especially useful for biomedical devices placed into contact with mucosal tissue. According to various preferred embodiments, the biomedical device is an ophthalmic device, intended for placement in contact with epithelial tissue, especially corneal onlays and contact lenses. The following disclosure references contact lenses, but is applicable to various other biomedical devices.

This invention is useful for all known types of contact lenses, including both soft and rigid lens materials. Hydrogels represent one class of materials used for contact lens applications. Hydrogels comprise a hydrated, cross-linked polymeric system containing water in an equilibrium state. Accordingly, hydrogels are copolymers prepared from hydrophilic monomers. In the case of silicone hydrogels, the hydrogel copolymers are generally prepared by polymerizing a mixture containing at least one device-forming silicone-containing monomer and at least one device-forming hydrophilic monomer. Either the silicone-containing monomer or the hydrophilic monomer may function as a crosslinking agent (a crosslinking agent being defined as a monomer having multiple polymerizable functionalities), or alternately, a separate crosslinking agent may be employed in the initial monomer mixture from which the hydrogel copolymer is formed. (As used herein, the term "monomer" or "monomeric" and like terms denote relatively low molecular weight compounds that are polymerizable by free radical polymerization, as well as higher molecular weight compounds also referred to as "prepolymers", "macromonomers", and related terms.) Silicone hydrogels typically have a water content between about 10 to about 80 weight percent.

Examples of useful lens-forming hydrophilic monomers include: amides such as N,N-dimethylacrylamide and N,N-dimethylmethacrylamide; cyclic lactams such as N-vinyl-2-pyrrolidone; (meth)acrylated alcohols, such as 2-hydroxyethyl methacrylate and 2-hydroxy ethylacrylate; and (meth)acrylated poly(ethyleneglycol)s; and azlactone-containing monomers, such as 2-isopropenyl-4,4-dimethyl-2-oxazolin-5-one and 2-vinyl-4,4-dimethyl-2-oxazolin-5-one. (As used herein, the term "(meth)" denotes an optional methyl substituent. Thus, terms such as "(meth)acrylate" denotes either methacrylate or acrylate, and "(meth)acrylic acid" denotes either methacrylic acid or acrylic acid.) Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277, the disclosures of which are incorporated herein by reference. Other suitable hydrophilic monomers will be apparent to one skilled in the art.

As mentioned, one preferred class hydrogel contact lens materials is silicone hydrogels. In this case, the initial lens-forming monomer mixture further comprises a silicone-containing monomer.

Applicable silicone-containing monomeric materials for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

Examples of applicable silicon-containing monomers include bulky polysiloxanylalkyl (meth)acrylic monomers.

An example of bulky polysiloxanylalkyl (meth)acrylic monomers are represented by the following Formula I:

$$\text{(I)}$$

wherein:
X denotes —O— or —NR—;
each $R_1$ independently denotes hydrogen or methyl;
each $R_2$ independently denotes a lower alkyl radical, phenyl radical or a group represented by $$-\underset{\underset{R_2'}{|}}{\overset{\overset{R_2'}{|}}{Si}}-R_2'$$

wherein each $R_2'$ independently denotes a lower alkyl or phenyl radical; and h is 1 to 10. One preferred bulky monomer is methacryloxypropyl tris(trimethyl-siloxy) silane or tris(t-rimethylsiloxy)silylpropyl methacrylate, sometimes referred to as TRIS.

Another class of representative silicon-containing monomers includes silicone-containing vinyl carbonate or vinyl carbamate monomers such as: 1,3-bis[4-vinyloxycarbonyloxy)but-1-yl]tetramethyl-disiloxane; 1,3-bis[4-vinyloxycarbonyloxy)but-1-yl]polydimethylsiloxane; 3-(trimethylsilyl)propyl vinyl carbonate; 3-(vinyloxycarbonylthio)propyl-[tris(trimethylsiloxy)silane]; 3-[tris(tri-methylsiloxy)silyl] propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; and trimethylsilylmethyl vinyl carbonate.

An example of silicon-containing vinyl carbonate or vinyl carbamate monomers are represented by Formula II:

$$\text{(II)}$$

wherein:
Y' denotes —O—, —S— or —NH—;
$R^{Si}$ denotes a silicone-containing organic radical;
$R_3$ denotes hydrogen or methyl;
d is 1, 2, 3 or 4; and q is 0 or 1.

Suitable silicone-containing organic radicals $R^{Si}$ include the following:

$$—(CH_2)_{n'}Si[(CH_2)_{m'}CH_3]_3; \quad —(CH_2)_{n'}Si[OSi(CH_2)_{m'}CH_3]_3;$$

wherein:
$R_4$ denotes $$—(CH_2)_{p'}—O—\underset{O}{\overset{}{\underset{\|}{C}}}—CH=CH_2$$

wherein p' is 1 to 6;
$R_5$ denotes an alkyl radical or a fluoroalkyl radical having 1 to 6 carbon atoms;
e is 1 to 200; n' is 1, 2, 3 or 4; and m' is 0, 1, 2, 3, 4 or 5.

An example of a particular species within Formula II is represented by Formula III:

$$\text{(III)}$$

Another class of silicon-containing monomers includes polyurethane-polysiloxane macromonomers (also sometimes referred to as prepolymers), which may have hard-soft-hard blocks like traditional urethane elastomers. Examples of silicone urethane monomers are represented by Formulae IV and V:

$$E(*D*A*D*G)_a*D*A*D*E'; \text{ or} \quad \text{(IV)}$$

$$E(*D*G*D*A)_a*D*G*D*E'; \quad \text{(V)}$$

wherein:
D denotes an alkyl diradical, an alkyl cycloalkyl diradical, a cycloalkyl diradical, an aryl diradical or an alkylaryl diradical having 6 to 30 carbon atoms;
G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;
* denotes a urethane or ureido linkage;
a is at least 1;
A denotes a divalent polymeric radical of Formula VI:

$$E-(CH_2)_{m'}-\left[\begin{array}{c}R_s\\|\\Si-O\\|\\R_s\end{array}\right]_p\begin{array}{c}R_s\\|\\Si-(CH_2)_{m'}-E'\\|\\R_s\end{array} \quad (VI)$$

wherein:
each $R_s$ independently denotes an alkyl or fluoro-substituted alkyl group having 1 to 10 carbon atoms which may contain ether linkages between carbon atoms;
m' is at least 1; and
p is a number which provides a moiety weight of 400 to 10,000;
each of E and E' independently denotes a polymerizable unsaturated organic radical represented by Formula VII:

$$\begin{array}{c}R_6\\ \\R_7\\ \diagdown\\ \diagup\\R_7\end{array}(CH_2)_w-(X)_x-(Z)_z-(Ar)_y-R_8- \quad (VII)$$

wherein:
$R_6$ is hydrogen or methyl;
$R_7$ is hydrogen, an alkyl radical having 1 to 6 carbon atoms, or a —CO—Y—$R_9$ radical wherein Y is —O—, —S— or —NH—;
$R_8$ is a divalent alkylene radical having 1 to 10 carbon atoms;
$R_9$ is a alkyl radical having 1 to 12 carbon atoms;
X denotes —CO— or —OCO—;
Z denotes —O— or —NH—;
Ar denotes an aromatic radical having 6 to 30 carbon atoms;
w is 0 to 6; x is 0 or 1; y is 0 or 1; and z is 0 or 1.
A more specific example of a silicone-containing urethane monomer is represented by Formula (VIII):

group, such as the diradical of isophorone diisocyanate, and each E" is a group represented by:

$$\begin{array}{c}CH_3\\|\\CH_2=C-C(=O)-O-CH_2-\end{array}$$

A preferred silicone hydrogel material comprises (based on the initial monomer mixture that is copolymerized to form the hydrogel copolymeric material) 5 to 50 percent, preferably 10 to 25, by weight of one or more silicone macromonomers, 5 to 75 percent, preferably 30 to 60 percent, by weight of one or more polysiloxanylalkyl (meth)acrylic monomers, and 10 to 50 percent, preferably 20 to 40 percent, by weight of a hydrophilic monomer. In general, the silicone macromonomer is a poly(organosiloxane) capped with an unsaturated group at two or more ends of the molecule. In addition to the end groups in the above structural formulas, U.S. Pat. No. 4,153,641 to Deichert et al. discloses additional unsaturated groups, including acryloxy or methacryloxy. Fumarate-containing materials such as those taught in U.S. Pat. Nos. 5,512, 205; 5,449,729; and 5,310,779 to Lai are also useful substrates in accordance with the invention. Preferably, the silane macromonomer is a silicon-containing vinyl carbonate or vinyl carbamate or a polyurethane-polysiloxane having one or more hard-soft-hard blocks and end-capped with a hydrophilic monomer.

An additional class of contact lens materials are rigid copolymers, especially rigid, gas-permeable (RGP) copolymers. RGP copolymers generally include: a silicone-containing monomer, including any of the aforementioned silicone-containing monomers mentioned above; a hydrophilic monomer as a wetting agent; a hardness modifying monomer; and a crosslinking agent; a polymerization initiator; an ultraviolet blocking agent; or a colorant.

Specific examples of contact lens materials useful in the present invention are taught in U.S. Pat. Nos. 6,891,010 (Kunzler et al.); 5,908,906 (Kunzler et al.); 5,714,557 (Kunzler et al.); 5,710,302 (Künzler et al.); 5,708,094 (Lai et al.); 5,616, 757 (Bambury et al.); 5,610,252 (Bambury et al.); 5,512,205 (Lai); 5,449,729 (Lai); 5,387,662 (Kunzler et al.); 5,310,779

$$E''-\left[\begin{array}{c}OCN-R_{10}-\underset{H}{N}\underset{\parallel}{C}OCH_2CH_2OCH_2CH_2O\underset{\parallel}{C}\underset{H}{N}-R_{10}-\underset{H}{N}\underset{\parallel}{C}O(CH_2)m\left(\begin{array}{c}CH_3\\|\\Si-O\\|\\CH_3\end{array}\right)_p\begin{array}{c}CH_3\\|\\Si-(CH_2)m\\|\\CH_3\end{array}\right]_a \quad (VIII)$$

$$E''-OCN-R_{10}-\underset{\parallel}{\underset{H}{N}}\underset{O}{C}OCH_2CH_2OCH_2CH_2O\underset{\parallel}{\underset{H}{C}}\underset{O}{N}-R_{10}-\underset{\parallel}{\underset{H}{N}}\underset{O}{C}O-$$

wherein m is at least 1 and is preferably 3 or 4, a is at least 1 and preferably is 1, p is a number which provides a moiety weight of 400 to 10,000 and is preferably at least 30, $R_{10}$ is a diradical of a diisocyanate after removal of the isocyanate (Lai); 5,260,000 (Nandu et al.); and 5,346,976 (Ellis et al.); the disclosures of which are incorporated herein by reference.

The polymers linked to the contact lens surface contain a moiety that complexes, or forms a complex, with mucin.

Boronic acid groups complex readily with sialic acid carbohydrate residues at physiological pH (7.4). Because mucins contain substantial amounts of sialic acid residues in their polysaccharide side chains, boronic acid groups should have an affinity for mucins. Preferred polymers contain a boronic acid moiety. Boronic acid ($—B(OH)_2$) groups are able to complex with the polysaccharide side chains found in mucin, and thereby possess an affinity for the mucins in tear fluid while the contact lens is worn.

The polymers may comprise monomeric units derived from an ethylenically unsaturated monomer containing the boronic acid moiety. Examples are ethylenically unsaturated aryl boronic acids, such as: 4-vinylphenyl boronic acid; and N-methacryloyl-3-amino-phenyl boronic acid.

The preferred polymers include, in addition to the monomeric units derived from an ethylenically unsaturated monomer containing the boronic acid moiety, a monomeric unit derived from an ethylenically unsaturated monomer containing a reactive moiety. Specifically, the ethylenic unsaturation of this monomer renders the monomer copolymerizable with the boronic acid-containing monomer. In addition, this monomer contains the reactive moiety that is reactive with complementary reactive functionalities at the lens surface, and/or complementary reactive functionalities of an intermediate polymer, discussed in more detail below.

Examples of reactive monomers include: ethylenically unsaturated carboxylic acids, such as (meth)acrylic acid; ethylenically unsaturated primary amines, such as ethylamino (meth)acrylate, ethylamino(meth)acrylamide, propylamino (meth)acrylate, and propylamino(meth)acrylamide; alcohol-containing (meth)acrylates and (meth)acrylamides, such as 2-hydroxyethyl methacrylate; ethylenically unsaturated epoxy-containing monomers, such as glycidyl methacrylate or glycidyl vinyl carbonate; and azlactone-containing monomers, such as 2-isopropenyl-4,4-dimethyl-2-oxazolin-5-one and 2-vinyl-4,4-dimethyl-2-oxazolin-5-one, where the azlactone group hydrolyzes in aqueous media to convert the oxazolinone moiety to a reactive carboxylic acid moiety.

The polymers may further include a monomeric unit containing a tertiary-amine moiety. Generally, diols complex most readily with mucins at a basic pH. By including this monomeric unit in the polymer, it is believed the boronic acid will complex more readily with mucin at physiological pH. Examples of monomers copolymerizable with the boronic acid monomer are ethylenically unsaturated monomers containing the tertiary-amine moiety. Specific examples include: 2-(N,N-dimethyl) ethylamino(meth)acrylate, 2-(N,N-dimethyl)ethylamino(meth)acrylamide, 3-(N,N-dimethyl)propylamino(meth)acrylate, 3-(N,N-dimethyl) propylamino (meth)acrylamide and vinylbenzyl-N,N-dimethylamine.

The polymers may further include a hydrophilic monomeric unit. Examples include ethylenically unsaturated monomers that are copolymerizable with the boronic acid ethylenically unsaturated monomer. Specific examples include: N,N-dimethylacrylamide and N,N-dimethylmethacrylamide; cyclic lactams such as N-vinyl-2-pyrrolidone; (meth)acrylated alcohols, such as 2-hydroxyethyl methacrylate and 2-hydroxyethylacrylate; and (meth)acrylated poly(ethyleneglycol)s. The main purpose of the hydrophilic monomeric unit in the polymer, when used, is to ensure the polymer is water-soluble, thus avoiding the need to dissolve the polymer in organic solvent when applying the polymer to the lens surface.

Accordingly, preferred polymers are copolymers comprising: monomeric units derived from an ethylenically unsaturated monomer containing a boronic acid moiety; and monomeric units derived from an ethylenically unsaturated monomer containing a moiety reactive with complementary reactive functionalities at the lens surface. These copolymers may further include: monomeric units derived from the ethylenically unsaturated monomer containing the tertiary-amine moiety; and monomeric units derived from an ethylenically unsaturated hydrophilic monomer in an amount sufficient to render the copolymer water soluble.

Preferably, the copolymers comprise: 1 to 30 mole percent of the boronic acid-containing monomeric units, more preferably 2 to 20 mole percent; and 2 to 50 mole percent of monomeric units derived from an ethylenically unsaturated monomer containing the moiety reactive with complementary reactive functionalities at the lens surface, more preferably 5 to 40 mole percent. Preferably, these copolymers comprise: 0 to 50 mole percent of the tertiary-amine-containing monomeric units, more preferably 5 to 40 mole percent; and 0 to 90 mole percent of the hydrophilic monomeric units, more preferably 20 to 80 mole percent.

As mentioned, the copolymers include monomeric units derived from an ethylenically unsaturated monomer containing a reactive moiety, and this reactive moiety links the polymer to the lens surface. One manner of linking the boronic acid-containing polymer to the lens surface involves forming the lens from a monomer mixture including a monomer that includes reactive functionalities that are complementary with the reactive moiety of the polymer.

As a first example, the contact lens may be formed of the polymerization product of a monomer mixture comprising an epoxy-containing monomer, such as glycidyl methacrylate or glycidyl vinyl carbonate. Sufficient epoxy groups will migrate to the lens surface, and these epoxy groups covalently react with functionalities of the boronic acid-containing polymer, especially carboxylic acid, amino and alcohol reactive moieties.

As a second example, the contact lens may be formed of the polymerization product of a monomer mixture comprising a carboxylic acid-containing monomer, such as (meth)acrylic acid or vinyl carbonic acid. Sufficient carboxylic groups will be present at the lens surface to covalently react with functionalities of the boronic acid-containing polymer, especially amino and alcohol reactive moieties.

As a third example, the contact lens may be formed of the polymerization product of a monomer mixture comprising an azlactone-containing monomer, such as 2-isopropenyl-4,4-dimethyl-2-oxazolin-5-one and 2-vinyl-4,4-dimethyl-2-oxazolin-5-one. Azlactone groups at the lens surface will hydrolyze in aqueous media to convert the oxazolinone group to a carboxylic acid, for reaction with the boronic acid-containing polymer reactive moieties.

As another example, the contact lens may be formed of the polymerization product of a monomer mixture comprising a (meth)acrylate or (meth)acrylamide alcohol, such as 2-hydroxyethyl methacrylate. The alcohol groups are available to react with boronic acid-containing polymer reactive moieties.

Other lens-forming monomers containing complementary reactive groups are known in the art, including those disclosed in U.S. Pat. No. 6,440,571 (Valint, Jr. et al.), the entire disclosure of which is incorporated herein by reference.

Another manner of linking the boronic acid-containing polymer to the lens surface involves treating the lens surface to provide reactive functionalities that are complementary with the reactive moiety of the polymer. As an example, the lens surface may be subjected to plasma treatment in an oxygen-containing atmosphere to form alcohol functionalities on the lens surface, or in a nitrogen-containing atmosphere to form amine functionalities on the lens surface. In the case that the contact lens contains fluorine at its surface, the lens surface may be initially plasma treated in a hydrogen atmosphere to reduce fluorine content at the lens surface. Such methods are known in the art, including U.S. Pat. Nos. 6,550,915 and 6,794,456 (Grobe III), the entire disclosures of which are incorporated herein by reference.

The alcohol or amino functionality generated at the lens surface by the plasma treatment may then react with reactive moieties of the boronic acid-containing polymer, especially carboxylic acid moieties.

A variation of plasma treatment involves initially subjecting the lens surface to a plasma oxidation, followed by plasma polymerization in an atmosphere containing a hydrocarbon (such as a diolefin, for example, 1,3-butadiene) to form a carbon layer on the lens surface. Then, this carbon layer is plasma treated in an oxygen or nitrogen atmosphere to generate hydroxyl or amine radicals. The reactive moiety of the boronic acid-containing polymer can then be covalently attached to the hydroxyl or amine radicals of the carbon layer. This method is disclosed in U.S. Pat. No. 6,213,604 (Valint, Jr. et al.), the entire disclosure of which is incorporated herein by reference.

As used herein, the term "plasma treatment" is inclusive of wet or dry corona discharge treatments.

Another manner of linking the boronic acid-containing polymer to the lens surface involves employing an intermediate polymer. More specifically, the intermediate polymer is linked to both the boronic acid-containing polymer and the lens surface. Thus, this intermediate polymer has functionality reactive with the lens surface, as well as functionality reactive with the reactive moieties of the boronic acid-containing polymer.

This intermediate polymer may be covalently linked to the lens surface by the various methods, discussed supra in relation to direct linking of the boronic acid-containing polymer. For example, the contact lens may be formed of a monomer mixture including a monomer that includes reactive functionalities that are complementary with the reactive functionalities of the intermediate polymer. Alternately, the contact lens surface may be treated, for example, plasma treated, to provide reactive sites for the intermediate polymer The intermediate polymer may be covalently linked to the boronic acid-containing polymer by providing both polymers with complementary reactive groups, including those mentioned supra. Additional examples are found in U.S. Pat. No. 6,440,571 (Valint, Jr. et al.).

As an example, the lens may be coated with a mixture of an intermediate copolymer of N,N-dimethylacrylamide and glycidyl methacrylate, and a boronic acid-containing copolymer. The epoxy functionality of the intermediate copolymer will covalently link to hydroxyl, primary amine or carboxylic acid moieties at the lens surface, and will covalently link to hydroxyl, primary amine or carboxylic acid moieties of the boronic acid-containing polymer. Numerous other examples of intermediate polymers are evident.

Accordingly, various methods generally known in the art are available for linking the boronic acid-containing polymer to the contact lens surface. Other methods will be evident to ones skilled in the art.

The following examples illustrate various preferred embodiments of this invention.

Example 1

Synthesis of Boronic Acid-Containing Polymer

To a 1-L 3-neck round bottom flask containing a magnetic stir bar, water-cooled condenser and thermocouple is added approximately 0.2-wt % AIBN initiator (based on total weight of monomers), 5.0-mol % of 4-vinylphenyl boronic acid (SBA), 10-mol % of methacrylic acid (MAA), 20-mol % of 3-(N,N-dimethylamino)propyl methacrylamide (DMAPMA) and 65-mol % of N,N-dimethylacrylamide (DMA). The monomers and initiator are dissolved by addition of 300-mL of methanol to the flask. The solution is sparged with argon for at least 10-min. before gradual heating to 60° C. Sparging is discontinued when the solution reaches 40 to 45° C. and the flask is subsequently maintained under argon backpressure. Heating is discontinued after 48 to 72 hours at which point the cooled solution is added dropwise to 5 L of mechanically stirred ethyl ether. The precipitate is isolated either by filtration or decanting off the ether. The solid is dried in vacuo at 40° C. for a minimum of 18 hours and reprecipitated by dissolution in 300-mL methanol and dropwise addition into 5-L of stirred ethyl ether. The final polymer mass is determined after vacuum drying at 40° C. to a constant mass.

Examples 2-12

Synthesis of Boronic Acid-Containing Polymers

The polymers in Table 1 were synthesized according to the general procedure of Example 1, by varying the molar amounts and various monomers. The following additional designations are used in Table 1:

| APMA | 3-aminopropyl methacrylamide |
| AEMA | 2-aminoethyl methacrylate |
| DMAEMA | 2-(N,N-dimethylamino)ethyl methacrylate |
| DMAPMA | 3-(N,N-dimethylamino)propyl methacrylamide |
| MAAPBA | N-methacryloyl-3-amino-phenyl boronic acid |

TABLE 1

|  | Ex 1 | Ex 2 | Ex 3 | Ex 4 | Ex 5 | Ex 6 |
|---|---|---|---|---|---|---|
| DMA (mol %) | 65 | 50 | 55 | 40 | 65 | 68.5 |
| DMAPMA (mol %) | 20 | 30 | 25 | 20 | — | 19 |
| DMAEMA (mol %) | — | — | — | — | 20 | — |
| MAA (mol %) | 10 | 10 | 10 | 30 | 10 | — |
| APMA (mol %) | — | — | — | — | — | 7.5 |
| SBA (mol %) | 5 | 10 | 10 | 10 | 5 | 5 |

|  | Ex 7 | Ex 8 | Ex 9 | Ex 10 | Ex 11 | Ex 12 |
|---|---|---|---|---|---|---|
| DMA (mol %) | 70 | 70 | 70 | 65 | 65 | 70 |
| DMAPMA (mol %) | — | 20 | 20 | 15 | 10 | 16 |
| DMAEMA (mol %) | 20 | — | — | — | — | — |
| MAA(mol %) | — | — | 7.5 | — | — | 7 |
| APMA (mol %) | — | 7.5 | — | 10 | 10 | — |
| AEMA (mol %) | 5 | — | — | — | — | — |
| SBA (mol %) | 5 | — | — | 10 | 15 | 7 |
| MAAPBA (mol %) | — | 2.5 | 2.5 | — | — | — |

Example 13

Coating of Contact Lenses with Boronic Acid-Containing Polymers

Contact lenses made of balafilcon A were cast and stored in borate buffer solution (BBS). Balafilcon A is a copolymer comprised of 3-[tris(tri-methylsiloxy)silyl] propyl vinyl carbamate, N-vinyl-2-pyrrolidone (NVP), 1,3-bis[4-vinyloxy-carbonyloxy)but-1-yl]polydimethylsiloxane and N-vinyloxycarbonyl alanine. The lenses were not plasma treated, and these lenses are designated as "No Plasma Control" in the following tables. Other balafilcon A lenses were plasma treated, and are designated "PV Control", below.

Some lenses of this batch were desalinated in deionized water, dried and subjected to successive plasma regimens of ammonia, butadiene and ammonia. Some lenses retained as further controls are designated "ABA Control" in the following tables.

For coating with the subject polymers, each ABA treated lens was placed in a glass scintillation vial containing 1.5-mL of a 2% (w/v) solution of the subject polymer dissolved in deionized water or phosphate buffered saline and 1.5 mL of a 1% (w/v) solution of DMA/GMA copolymer (86/14 mol/mol) in deionized water. The vials were capped and placed in a forced-air oven heated to 90° C. for 2 hours. After cooling, the coating solution was removed by aspiration and replaced with 20-mL of deionized (DI) water with shaking. After two additional aspiration/irrigation cycles, the lenses were sealed in polypropylene contact lens blister packs in BBS. The blister packs were autoclaved at 121° C. for 30-min.

Table 2 reports various surface properties of several coated samples and controls. Coated sample 1 was coated with the polymer of Example 1, and Coated sample 2 was coated with the polymer of Example 9. Atomic concentrations were determined by XPS, as described below. Contact angle was determined as described below.

analyzed utilizing a low-resolution survey spectra (0-1100 eV) to identify the elements present on the sample surface. Quantification of elemental compositions was completed by integration of the photoelectron peak areas. Analyzer transmission, photoelectron cross-sections and source angle correction were taken into consideration in order to give accurate atomic concentration values.

Contact Angle Analysis

The instrument used for measurement was a Video Contact Angle System (VCA) 2500XE, (AST Products, Inc., Billerica, Mass. U.S.A.). This instrument utilizes a low-power microscope that produces a sharply defined image of the water drop, which is captured immediately on the computer screen. HPLC water is drawn into the VCA system microsyringe, and a 0.6 µl drop is dispensed from the syringe onto the sample. The contact angle is calculated by placing five markers along the circumference of the drop. The software of the system calculates a curve representing the circumference of the drop and the contact angle is recorded. Both a right and left contact angle are reported for each measurement in Table 2.

Protein Uptake Analysis

Table 3 reports protein uptake of lenses. The sample and control lenses were coated individually using a protein deposition solution (515 ppm standard) containing lysozyme. Glass vials containing 0.75 mL of deposition solution and individual lenses were placed into a 37° C. oven. After incu-

TABLE 2

| | XPS Atomic Concentrations | | | | Contact Angle |
|---|---|---|---|---|---|
| | % C | % O | % N | % Si | (Water) |
| Coated Sample 1 | 69.6 +/− 0.6 | 17.1 +/− 0.4 | 11.3 +/− 0.6 | 0.3 +/− 0.1 | 73/81 |
| ABA Control 1 | 67.4 +/− 3.7 | 17.8 +/− 1.9 | 8.4 +/− 0.6 | 6.1 +/− 2.2 | 83/75 |
| No Plasma Control 1 | 60.2 +/− 0.4 | 21.3 +/− 0.3 | 7.6 +/− 0.4 | 10.9 +/− 0.6 | 115/117 |
| Coated Sample 2 | 70.2 +/− 1.7 | 16.5 +/− 0.8 | 11.9 +/− 0.5 | 0.7 +/− 0.2 | 47/40 |
| ABA Control 2 | 64.8 +/− 4.8 | 19.4 +/− 2.4 | 7.7 +/− 1.0 | 7.7 +/− 1.4 | 94/74 |
| No Plasma Control | 59.4 +/− 0.3 | 22.1 +/− 0.2 | 7.1 +/− 0.2 | 11.3 +/− 0.2 | 111/115 |

X-ray Photoelectron Spectroscopy (XPS) Analysis

XPS data was collected using a Physical Electronics Quantera SXM Scanning ESCA Microprobe. This instrument utilizes a monochromatic Al anode operated at 18 kV and 100 Watts in the high power mode and 15 kV and 0.25 Watts/micron in low power mode. All high power acquisitions are rastered over a 1400 micron×100 micron analysis area. Dual beam neutralization (ions and electrons) is used. The base pressure of the instrument was $5 \times 10^{-10}$ torr and during operation the pressure was less than or equal to $1 \times 10^{-7}$ torr. This instrument made use of a hemispherical analyzer operated in FAT mode. A gauze lens was coupled to a hemispherical analyzer in order to increase signal throughput. Assuming the inelastic mean free path for a carbon 1 s photoelectron is 35 Å, the practical measure for sampling depth for this instrument at a sampling angle of 45 is approximately 75 Å. The governing equation for sampling depth in XPS is:

$$\theta \lambda \sin 3 = d$$

where d is the sampling depth, λ is the photoelectron inelastic mean free path and θ is the angle formed between the sample surface and the axis of the analyzer. Each specimen was bating for twenty-four hours, the vials containing the lenses were removed from the oven. Each lens was removed from the vial using tweezers and rinsed with saline solution. The deposition solution/standard, and the solution in which the lenses were incubated, were run by liquid chromatography (LC). The average of each set of lenses was established and the difference between the deposition solution and the lens incubation solution calculated. The same procedure was applied to the sample lenses. LC analysis was conducted using an Agilent 1100 Series Liquid Chromatograph, with the following instrument parameters:

| | |
|---|---|
| Column: | 4.6 mm × 150 mm Zorbax 300SB-C5, 5µ particle size |
| Mobile Phase A: | 95% HPLC Water/5% HPLC Acetonitrile with 0.1% TFA |
| Mobile Phase B: | 95% HPLC Acetonitrile/5% HPLC Water with 0.1% TFA |
| Gradient: | 85% A to 47% A over 20 minutes, reset to initial conditions, hold 10 minutes |

-continued

| Flow Rate: | 1 mL/minute |
|---|---|
| Injection Volume: | 10.0 µL |
| UV Detection: | 215 nm |

TABLE 3

| | Protein Uptake (µg/lens) |
|---|---|
| Coated Sample 1 | 23 +/− 4 |
| Coated Sample 2 | 20 +/− 1 |
| PV Control | 20 +/− 4 |

Example 14

Mucin Affinity

Mucin affinity was evaluated using an enzyme linked lectin assay. This assay utilizes biotinylated jacalin as a probe for detection of mucin on the contact lens surface. The strong biotin-streptavidin interaction provides the base for further signal amplification using a streptavidin-peroxidase conjugate.

Coated Samples 1 and 2 from Example 13 were evaluated, as well as two controls, PV Control and No Plasma Control from Example 13.

To test the mucin affinity of the contact lens material, purified Bovine Submaxillary Gland Mucin (BSM) was used. The mucin solution was prepared at 0.5 mg/ml using a 20 mM PBS buffer (PBS20; pH 7.4; Na/K=33). The contact lenses were stored at room temperature prior to analysis. First, the lenses were washed with PBS20 and transferred with a tweezer to a vial containing the mucin solution. Incubation with the coating solution proceeded over night at room temperature. Remaining uncoated spots on the samples were blocked using the synthetic surfactant Pluronic F108. Biotinylated jacalin was added to each vial and the samples were incubated at room temperature. This was followed by addition of streptavidin-peroxidase conjugate. Relative amount of bound mucin was quantified by the addition of substrate, followed by measurement of the degradation product at 405 nm.

Figure 1:
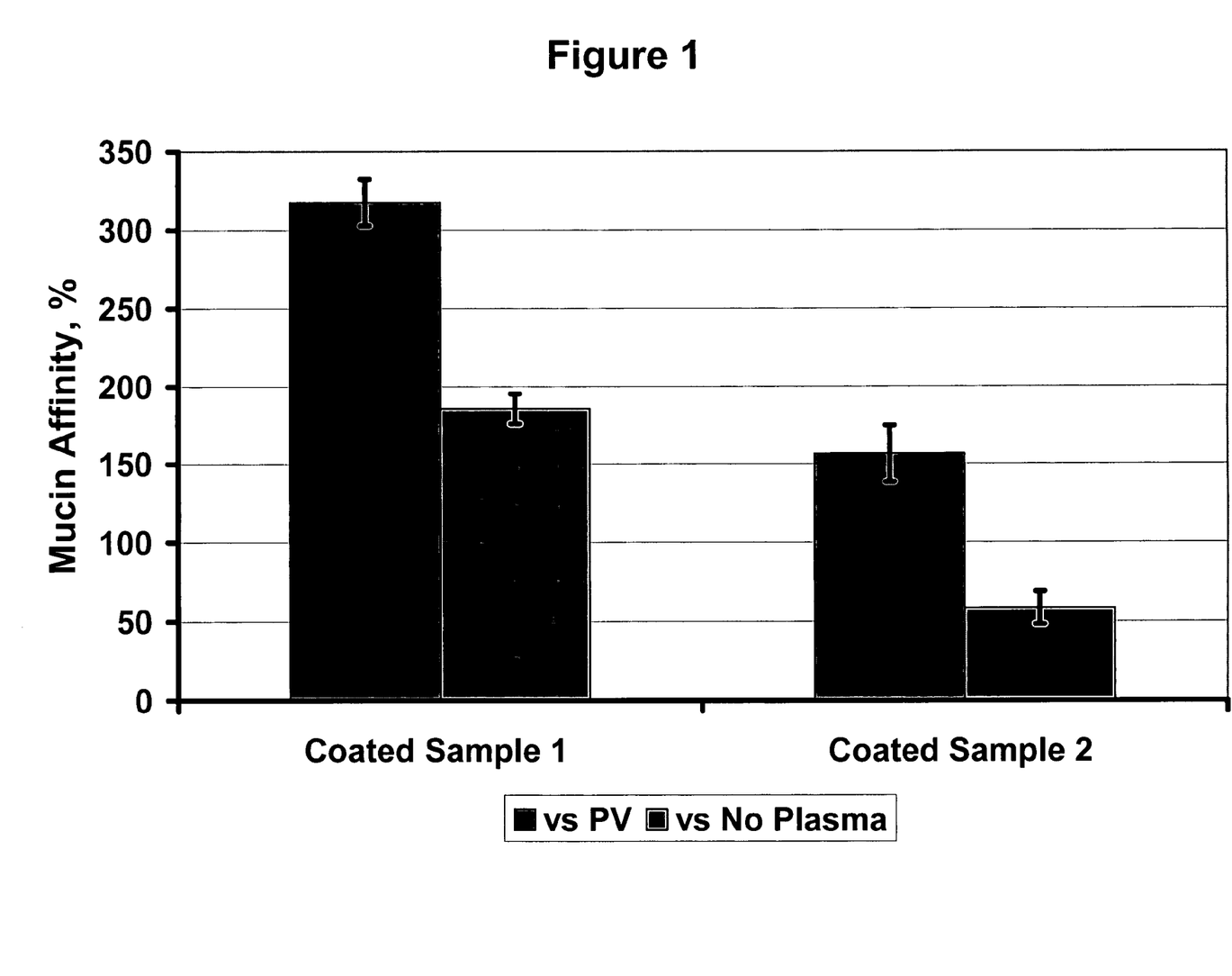

FIG. 1 shows the relative amount of bound mucin compared to both controls for each of the two samples. The absorbance of the enzyme degradation product was measured after a development time of three minutes. Comparing FIG. 1 with Table 3, it can be seen that the coated samples had greater affinity for mucin than for lysozyme.

Example 15

Copolymer of DMA/GMA (86/14 mol/mol)

The DMA/GMA copolymer of Example 13 was prepared by the following procedure. To a 1 L reaction flask were added distilled N,N-dimethylacrylamide (DMA, 48 g, 0.48 moles), distilled glycidyl methacrylate (GMA, 12 g, 0.08 moles) Vazo 64 initiator (AIBN, 0.1 g, 0.0006 moles) and anhydrous tetrahydrofuran (500 ml). The reaction vessel was fitted with a mechanical stirrer, condenser, thermal controller and a nitrogen inlet. Nitrogen was bubbled through the solution for 15 minutes to remove any dissolved oxygen. The reaction flask was then heated to 40° C. under a passive blanket of nitrogen for 168 hours. The reaction mixture was then added slowly to ethyl ether (1.5 L) with good mechanical stirring. The reactive polymer precipitated and organic solvents were decanted off. The solid was collected by filtration and placed in a vacuum oven to remove the ether leaving 58.2 g of reactive polymer (97% yield). The reactive polymer was placed in a desiccator for storage until use.

Examples 16-21 illustrate syntheses of other water-soluble copolymers that may be used to link the boronic acid-containing polymer to a lens surface.

Example 16

Copolymer of DMA/GMA (76/24 mol/mol)

To a 1 L reaction flask were added distilled N,N-dimethylacrylamide (DMA, 42 g, 0.42 moles), distilled glycidyl methacrylate (GMA, 18 g, 0.13 moles) Vazo 64 initiator (AIBN, 0.096 g, 0.0006 moles) and toluene (600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 6 L of ethyl ether with good mechanical stirring. The reactive polymer precipitated and was collected by vacuum filtration. The solid was placed in a vacuum oven at 30° C. overnight to remove the ether leaving 46.7 g of reactive polymer (78% yield). The reactive polymer was placed in a desiccator for storage until use.

Example 17

Copolymer of DMA/GMA (68/32 mol/mol)

To a 1 L reaction flask were added distilled N,N-dimethylacrylamide (DMA, 36 g, 0.36 moles), distilled glycidyl methacrylate (GMA, 24 g, 0.17 moles) Vazo 64 initiator (AIBN, 0.096 g, 0.0006 moles) and toluene (600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 6 L of ethyl ether with good mechanical stirring. The reactive polymer precipitated and was collected by vacuum filtration. The solid was placed in a vacuum oven at 30° C. overnight to remove the ether leaving 49.8 g of reactive polymer (83% yield). The reactive polymer was placed in a desiccator for storage until use.

Example 18

Copolymer of DMA/OFPMA/GMA (84/1.5/14.5 mol/mol/mol)

To a 3000 ml reaction flask were added distilled N,N-dimethylacrylamide (DMA, 128 g, 1.28 moles), 1H,1H,5H-octafluoropentylmethacrylate (OFPMA, 8 g, 0.024 moles), distilled glycidyl methacrylate (GMA, 32 g, 0.224 moles) Vazo-64 initiator (AIBN, 0.24 g, 0.00144 moles) and tetrahydrofuran (2000 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 12 L of ethyl ether with good mechanical stirring. The reactive polymer precipitated and was collected by vacuum filtration. The solid was placed in a vacuum oven at 30° C. overnight to remove the ether leaving 134.36 g of reactive polymer (80% yield). The reactive polymer was placed in a desiccator for storage until use.

Example 19

Copolymer of DMA/OFPMA/GMA (85/0.18/14.82 mol/mol/mol)

To a 500 ml reaction flask were added distilled N,N-dimethylacrylamide (DMA,16 g, 0.16 moles), 1H,1H,5H-octafluoropentylmethacrylate (OFPMA, 0.1 g, 0.0003 moles, used as received), distilled glycidyl methacrylate (GMA, 4 g, 0.028 moles) Vazo-64 initiator (AIBN, 0.063 g, 0.00036 moles) and tetrahydrofuran (300 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 3 L of ethyl ether with good mechanical stirring. The reactive polymer precipitated and was collected by vacuum filtration. The solid was placed in a vacuum oven at 30° C. overnight to remove the ether leaving 14.5 g of reactive polymer (69 yield). The reactive polymer was placed in a desiccator for storage until use.

Example 20

Copolymer of DMA/LMA/GMA (84/1.5/14.5 mol/mol/mol)

To a 1000 ml reaction flask were added distilled N,N-dimethylacrylamide (DMA, 32 g, 0.32 moles), laurylmethacrylate (LMA, 1.5 g, 0.006 moles, used as received), distilled glycidyl methacrylate (GMA, 8 g 0.056 moles) Vazo-64 initiator (AIBN, 0.06 g, 0.00036 moles) and tetrahydrofuran (600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 3 L of ethyl ether with good mechanical stirring. The reactive polymer precipitated and was collected by vacuum filtration. The solid was placed in a vacuum oven at 30° C. overnight to remove the ether leaving 29.2 g of reactive polymer (70% yield). The reactive polymer was placed in a desiccator for storage until use.

Example 21

Copolymer of NVP/VCHE (85/15 mol/mol)

To a 1 L reaction flask were added distilled N-vinyl-2-pyrrolidinone (NVP, 53.79 g, 0.48 moles), 4-vinylcyclohexyl-1,2-epoxide (VCHE, 10.43 g, 0.084 moles), Vazo 64 (AIBN, 0.05 g, 0.0003 moles) and THF (600 ml). The reaction vessel was fitted with a magnetic stirrer, condenser, thermal controller and a nitrogen inlet. Nitrogen was bubbled through the solution for 15 minutes to remove any dissolved oxygen. The reaction flask was then heated to 60° C. under a passive blanket of nitrogen for 20 hours. The reaction mixture was then added slowly to 6 L of ethyl ether with good mechanical stirring. The copolymer precipitated and was collected by vacuum filtration. The solid was placed in a vacuum oven at 30° C. overnight to remove the ether leaving 21 g of reactive polymer (a 32% yield). The reactive polymer was placed in a desiccator for storage until use.

Having thus described various preferred embodiment of the invention, those skilled in the art will appreciate that various modifications, additions, and changes may be made thereto without departing from the spirit and scope of the invention, as set forth in the following claims.

We claim:

1. An ophthalmic device comprising a surface coated with a polymer comprising boronic acid moieties and complexing with epithelial mucin.

2. The ophthalmic device of claim 1, which is a contact lens.

3. The contact lens of claim 2, wherein the polymer comprises monomeric units derived from an ethylenically unsaturated monomer containing a boronic acid moiety.

4. The contact lens of claim 3, wherein the polymer comprises monomeric units derived from at least one member selected from the group consisting of: a vinylphenyl boronic acid and a methacrylamido phenyl boronic acid.

5. The contact lens of claim 4, wherein the polymer further comprises monomeric units derived from an ethylenically unsaturated hydrophilic monomer.

6. The contact lens of claim 4, wherein the polymer further comprises monomeric units derived from an ethylenically unsaturated monomer containing a tertiary-amine moiety.

7. The contact lens of claim 6, wherein the ethylenically unsaturated monomer is a 2-(N,N-dimethyl)ethylamino (meth)acrylate, a 2-(N,N-dimethyl)ethylamino(meth)-acrylamide, a 2-(N,N-dimethyl)propylamino(meth)acrylate; a 3-(N,N-dimethyl)propylamino(meth)acrylamide, or a vinylbenzyl-N,N-dimethylamine.

8. The contact lens of claim 2, wherein the polymer further comprises monomeric units derived from an ethylenically unsaturated monomer containing a moiety reactive with complementary reactive functionalities at the lens surface.

9. The contact lens of claim 8, wherein the polymer is covalently linked to the lens surface with the moiety reactive with the complementary functionality at the lens surface.

10. The contact lens of claim 2, wherein the polymer is a copolymer comprising: monomeric units derived from an ethylenically unsaturated monomer containing a boronic acid moiety; and monomeric units derived from an ethylenically unsaturated monomer containing a moiety reactive with complementary reactive functionalities at the lens surface.

11. The contact lens of claim 10, wherein the polymer is a copolymer further comprising monomeric units derived from an ethylenically unsaturated monomer containing a tertiary-amine moiety.

12. The contact lens of claim 11, wherein the polymer is a copolymer further comprising monomeric units derived from an ethylenically unsaturated hydrophilic monomer in an amount sufficient to render the copolymer water soluble.

13. The contact lens of claim 2, wherein the polymer is covalently bound to the lens surface through primary amine or hydroxyl radicals at the lens surface.

14. The contact lens of claim 2, wherein the polymer comprising boronic acid moieties is linked to the lens surface with an intermediate polymer reactive with both the lens surface and the polymer comprising boronic acid moieties.

15. The contact lens of claim 14, wherein the intermediate polymer is covalently linked to the lens surface and to the polymer comprising boronic acid moieties.

16. The contact lens of claim 14, wherein the polymer is a copolymer comprising: monomeric units derived from an ethylenically unsaturated monomer containing a boronic acid moiety; and monomeric units derived from an ethylenically unsaturated monomer containing a moiety reactive with complementary reactive functionalities of the intermediate polymer.

17. The contact lens of claim 16, wherein the polymer is a copolymer further comprising monomeric units derived from an ethylenically unsaturated monomer containing a tertiary-amine moiety.

18. The contact lens of claim 17, wherein the polymer is a copolymer further comprising monomeric units derived from an ethylenically unsaturated hydrophilic monomer in an amount sufficient to render the copolymer water soluble.

19. A method comprising coating a surface of an ophthalmic device with a polymer comprising boronic acid moieties, and placing the ophthalmic device in the eye, whereby epithelial mucin complexes with the polymer comprising boronic acid moieties.

20. The method of claim 19, wherein the biomedical device is a contact lens.

21. The method of claim 20, comprising placing the contact lens in the eye, whereby epithelial mucin complexes with the polymer comprising boronic acid moieties.

22. The method of claim 20, wherein the polymer comprises reactive moieties that are covalently linked to complementary reactive functionalities on the lens surface.

23. The method of claim 20, further comprising subjecting the surface of the lens to a plasma treatment that provides the complementary reactive functionalities on the lens surface.

24. The method of claim 20, wherein an intermediate polymer is linked to the lens surface, and the polymer comprising boronic acid moieties is linked to the intermediate polymer.

25. The method of claim 24, wherein the intermediate polymer is reactive with reactive functionality on the lens surface and reactive functionalities on the polymer comprising boronic acid moieties.

26. The method of claim 20, further comprising subjecting the surface of the lens to a plasma treatment that provides complementary reactive functionalities on the lens surface for the intermediate polymer.

27. An ophthalmic device coated with a copolymer comprising moieties that complex with epithelial mucin, said copolymer having greater affinity to epithelial mucin than to lysozyme.

28. The ophthalmic device of claim 27, which is a contact lens.

29. The ophthalmic device of claim 27, which is a contact lens coated with a copolymer comprising boronic acid moieties.

* * * * *